United States Patent [19]

Reich

[11] 4,262,522

[45] Apr. 21, 1981

[54] METHOD AND ARRANGEMENT FOR OPERATING GAS EXAMINING APPARATUSES

[75] Inventor: Günter Reich, Cologne, Fed. Rep. of Germany

[73] Assignee: Leybold-Heraeus GmbH, Cologne, Fed. Rep. of Germany

[21] Appl. No.: 33,337

[22] Filed: Apr. 25, 1979

[30] Foreign Application Priority Data

Jun. 23, 1978 [DE] Fed. Rep. of Germany ....... 2827537

[51] Int. Cl.³ ............................................. G01N 1/26
[52] U.S. Cl. ........................................ 73/23; 73/1 G; 73/421.5 R
[58] Field of Search ............. 73/19, 23, 1 G, 421.5 R; 250/288

[56] References Cited

U.S. PATENT DOCUMENTS

| | | | |
|---|---|---|---|
| 3,427,862 | 2/1969 | Hubner | 73/23 |
| 3,531,980 | 10/1970 | Pennucci | 73/19 |
| 3,537,296 | 11/1970 | Gamache | 73/23 |
| 3,921,457 | 11/1975 | Barnes et al. | 73/421.5 R |

FOREIGN PATENT DOCUMENTS

| | | |
|---|---|---|
| 1124730 | 4/1969 | Fed. Rep. of Germany . |
| 1573515 | 3/1971 | Fed. Rep. of Germany . |
| 2223258 | 12/1972 | Fed. Rep. of Germany . |
| 23771 | of 1903 | United Kingdom ....................... 73/23 |
| 1121853 | 7/1968 | United Kingdom . |
| 1309574 | 3/1973 | United Kingdom . |
| 1343011 | 1/1974 | United Kingdom . |

*Primary Examiner*—James J. Gill
*Attorney, Agent, or Firm*—Spencer & Kaye

[57] ABSTRACT

A method of operating a gas examining apparatus which has a gas examining device such as a mass spectrometer, a chamber communicating with the gas examining device, a gas pump communicating with the chamber and a probe hose coupled to the chamber for introducing into the apparatus gas to be examined. According to the method, in case probe hoses of different lengths or different quantities are used, the gas examination is so performed that the pressure in the above-mentioned chamber arranged upstream of the gas examining apparatus is maintained constant.

12 Claims, 4 Drawing Figures

METHOD AND ARRANGEMENT FOR OPERATING GAS EXAMINING APPARATUSES

BACKGROUND OF THE INVENTION

This invention relates to a method of operating an apparatus into which gases are introduced for purposes of, for example, leak detection or gas analysis. The gas to be examined by the apparatus is admitted thereto from one or more locations in one or several probe hoses which open into a chamber. The chamber is connected with the gas examining apparatus with the intermediary of a throttle and is further coupled to a vacuum pump or a delivery pump.

A gas examining apparatus of the above-outlined type which is provided with a sole probe hose is disclosed in German Offenlegungsschrift (Laid-Open Application) No. 2,441,124, to which corresponds British Pat. No. 1,489,953. The apparatus has the advantage that it has short periods of response and a high degree of sensitivity.

When working with gas examining apparatuses, such as leak detectors or gas analyzers, it is frequently necessary to use probe hoses of different lengths because often the apparatus, such as a leak detector, cannot be brought next to the container or the locations to be tested. For this reason, the gas examining apparatuses are, as a rule, marketed with a plurality of probe hoses of different lengths. It further may be necessary, for example, in case of testing several welds in the same operation, to simultaneously couple a plurality of probe hoses of identical or different lengths to the apparatus for a simultaneous examination of the gases flowing through the probes.

The use of conventional apparatuses of the above-outlined type involves the disadvantage that the results based on tests performed with probe hoses of different lengths or quantities cannot be compared with one another. Stated differently, if, for example, probe hoses of different lengths are used, identical leakage rates or gas concentrations which are in fact identical, are indicated by the apparatus as being different from one another. If now it is desired to obtain comparable measuring results with probe hoses of different lengths or different quantities, each time the hose arrangement is changed, it is necessary to recalibrate the apparatus, which is a time-consuming procedure.

SUMMARY OF THE INVENTION

It is an object of the invention to provide an improved method and arrangement of the above-outlined type which performs a gas examination (such as leakage detection or gas analysis) independently from the length and number of the probe hoses used.

This object and others to become apparent as the specification progresses, are accomplished by the invention, according to which, briefly stated, in case probe hoses of different lengths or different quantities are used, the gas examination is so performed that the pressure in the above-mentioned chamber arranged upstream of the gas examining apparatus is maintained constant.

This step provides that the flow rate of the gas which is to be tested and which is admitted to the gas examining apparatus always remains the same independently from the length or the number of the probe hoses. Consequently, the sensitivity of the gas examining apparatus remains independent from the length or the number of the probe hoses.

The gas examining apparatus preferably comprises a mass spectrometer. It is to be understood, however, that the invention may find application in examining apparatuses whose operation is based on a system other than a mass spectrometer.

The objective—namely, the supply of gas at unchanging flow rates—can be achieved by various means. Thus, according to a preferred embodiment, in order to maintain a constant pressure in the chamber when probe hoses of different lengths or quantities are used, the suction output of the vacuum pump coupled to the chamber is regulated. Such a regulation can be effected, for example, either by setting the vacuum pump proper or with the aid of an adjustable throttle valve inserted in the coupling conduit between the chamber and the vacuum pump.

According to another preferred embodiment, probe hoses of different diameters are used. The diameters are so selected that the diameter of the relatively long probe hoses is larger than that of the relatively short probe hoses. If unlike quantities of probe hoses are used, the invention can be practiced by ensuring that the sum of the conductance of the probe hoses always remains the same or by ensuring that the total flow rate of the gas passing through the unlike number of hoses remains the same. It is further feasible to connect the probe hoses proper to the chamber with the intermediary of an adjustable throttle valve.

DESCRIPTION OF THE PREFERRED EMBODIMENTS

Figure 1:
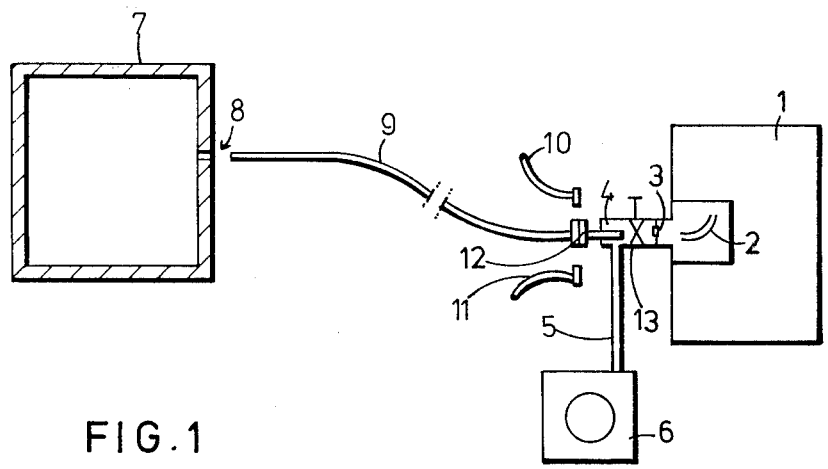
FIGS. 1 through 4 are schematic illustrations of four preferred embodiments of the invention.

In all the Figures there is symbolically shown a device 1 which is, for example, a leak detector and which is supplied with the gas to be examined. In the apparatus 1 there is arranged, for example, a mass spectrometer 2 which is set for the type of test gas used (such as helium, argon, chlorofluorocarbons or the like). A throttle 3 which may be a porous body, a slotted mask, a diaphragm or a nozzle, is arranged immediately upstream of the mass spectrometer 2. The throttle 3 may be of the adjustable type for pre-setting the desired sensitivity of the apparatus.

The throttle 3 separates the space, in which the mass spectrometer 2 is disposed, from a chamber 4 which communicates with a vacuum pump 6 by means of a conduit 5. The gases which are drawn by means of the vacuum pump 6 from the zone of a container 7 which is to be tested for leaks, are advanced to the chamber 4 in probe hoses. The container 7 has, for example, a leak 8. It has been found to be particularly advantageous if the chamber 4 has an as small volume as possible, expediently less than 3 $cm^3$ in case of a probe hose diameter of approximately 0.5 to 1 mm and a probe hose length of approximately 3 to 6 m. Such an arrangement ensures that even in case of relatively long probe hose lengths, the delay of response is small (in the range of several tenths of a second).

In the arrangement illustrated in FIG. 1, there are provided three probe hoses 9, 10 and 11 which have different lengths and which can be selectively and individually connected to the chamber 4 by means of a coupler 12. Dependent upon their lengths, the probe hoses have different diameters; the relatively long hoses have a relatively larger diameter than the relatively short hoses. This ensures that the pressure in the chamber 4 remains constant despite the different length of the probe hoses.

In the embodiment according to FIG. 1, communication between the chamber 4 and the space in which the mass spectrometer 2 is located can be interrupted by means of a valve 13. The use of the shut-off valve 13 has the advantage that the vacuum pump 6, when it is to be de-energized, can be shut off without causing a pressure increase in the space where the mass spectrometer 2 is situated when the pressure in the chamber 4 increases.

During operation, thus during, for example, a leak detection, the chamber 4 is maintained at a pressure which is lower than the atmospheric pressure. This ensures that gas is drawn at high speeds through the operative probe hose 9, while the receptacle 7 is scanned with the free end of the probe hose 9. Should the receptacle 7 contain, for example, a leak 8, test gas escapes from the receptacle through the leak and, at the moment the free end of the probe hose is brought into the zone of the leak, enters the probe and is advanced to the throttle 3. One part of the gas flows past the throttle 3 and enters the mass spectrometer 2, while the other part of the gas is drawn away by the vacuum pump 6.

Instead of the probe hose 9, the probe hoses 10 or 11, whose lengths differ from one another and from the probe hose 9, may be coupled to the chamber 4. Since the diameter of the probe hoses is so selected that the pressure prevailing in the chamber 4 does not vary, the sensitivity of the leak detector remains the same as well.

Figure 2:
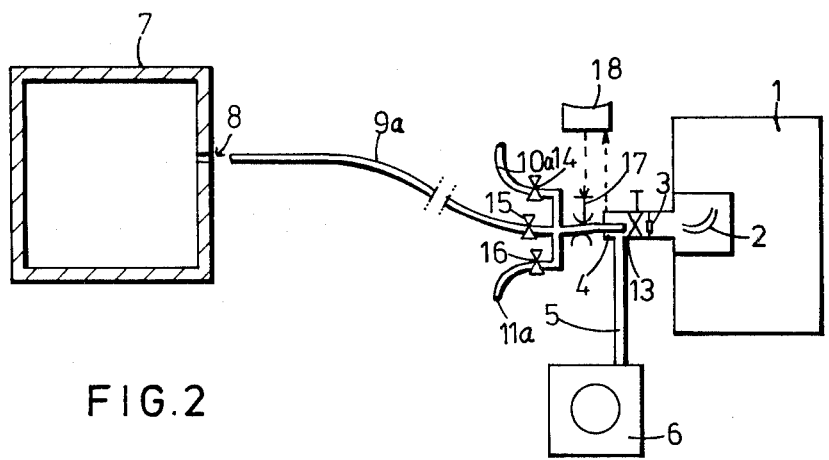

Turning now to the embodiment illustrated in FIG. 2, the probe hoses 9a, 10a and 11a are coupled to the chamber 4 with the interposition of valves 14, 15 and 16, respectively. In this embodiment the diameters of the probe hoses are the same, while their lengths are different, as in the earlier-discussed embodiment. In order to ensure that in such an arrangement there is maintained a constant pressure in the chamber 4, independently from the probe hose lengths, an adjustable throttle valve 17 is provided between the chamber, on the one hand, and the operative probe hose, on the other hand. The throttle valve 17 has to be so set that the selected pressure in the chamber 4 remains constant independently from the length of the momentarily attached probe hose. Such an adjustment can be effected, for example, by means of a regulator device 18 which sets the throttle valve 17 as a function of the pressure prevailing in the chamber 4. Such an arrangement is conventional by itself and is described, for example, in the catalogue HV250 of the firm Leybold-Heraeus (Kön, Germany), part 76/V6.1.2., section 6, page 6.22.

Figure 3:
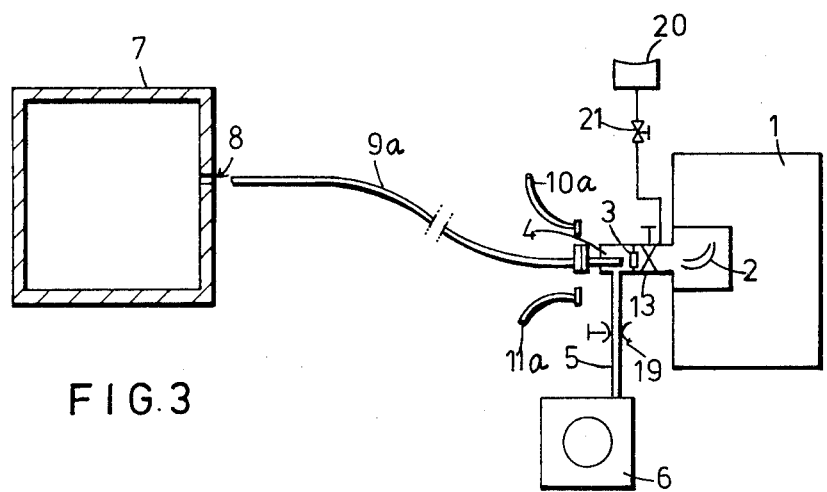

According to the embodiment illustrated in FIG. 3 there is provided an adjustable throttle valve 19 in the coupling conduit 5 leading to the vacuum pump 6 from the chamber 4. Similarly to the FIG. 2 embodiment, the throttle valve 19 can be controlled as a function of the pressure in the chamber 4 so that the pressure prevailing in the chamber 4 may be maintained at a constant value independently from the dimensions of the selected, operative probe hose. The arrangement shown in FIG. 3 further includes a test gas supply (test leak) 20 which, by means of a valve 21, can be coupled directly to the space in which the mass spectrometer 2 is situated. During the testing period or during calibration, the chamber 4 is disconnected from the gas examining apparatus by closing the valve 13.

In the embodiments shown in FIGS. 1 and 2, as viewed in the direction of gas flow towards the mass spectrometer 2, the valve 13 is arranged upstream of the throttle 3 whereas in the embodiment according to FIG. 3, it is situated downstream thereof. The arrangement according to FIGS. 1 and 2 has the advantage that, for example, upon replacement of the probe hoses and the inherent increase of the pressure in the chamber 4, the throttle 3 is protected from soiling. It is a disadvantage, however, that the test gas which still dwells between the valve 13 and the throttle 3, cannot flow away immediately, so that the indicator of the leak detector does not return immediately to zero. Such an immediate zero indication is, however, the case in the arrangement according to FIG. 3. This embodiment, in turn, is disadvantageous in that, for example, during replacement of the probe hoses, the pressure between the throttle 3 and the valve 13 increases to the atmospheric pressure and upon completion of the hose exchange, the pressure can be reduced only slowly, since the evacuation of this space can be effected only by the vacuum pump 6 as the valve 13 is closed. In both instances it is therefore essential that the throttle 3 and the valve 13 be situated as close to one another as possible to reduce the dead space between them to a minimum value. It is particularly advantageous to so construct the components 3 and 13 that they form a single structural unit.

Figure 4:
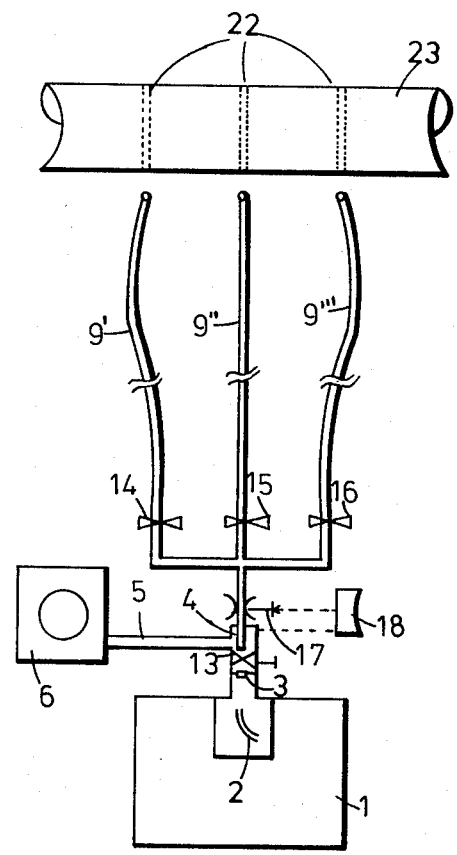

Turning now to FIG. 4, in the embodiment shown therein simultaneously several probe hoses 9', 9" and 9"' can be attached to the chamber 4 so that simultaneously several weld seams 22 of a tube 23 may be examined for leaks. The probe hoses 9', 9" and 9"' may have identical dimensions. If in such an arrangement the number of the attached hoses is altered then, in accordance with the invention, it has to be ensured that the pressure in chamber 4 remains constant. This is achieved by means of the control valve 17 and the regulator device 18, in a manner set forth in connection with FIG. 2. In the alternative, in the embodiment shown in FIG. 4 it is feasible to maintain the sum of the conductances of the simultaneously operating probe hoses constant.

It is to be understood that the above description of the present invention is susceptible to various modifications, changes and adaptations, and the same are intended to be comprehended within the meaning and range of equivalents of the appended claims.

What is claimed is:

1. In a method of operating a gas examining apparatus including a gas examining means; a chamber communicating with the gas examining means, a gas pump communicating with the chamber; and probe hoses of given length values and quantity values adapted to communicate with the chamber for introducing into the apparatus gas to be examined; said chamber being arranged upstream of said gas examining means as viewed in the direction of gas flow; the method including, in a measuring operation, the step of selectively using probe hoses differing from one another at least in one of said values; the improvement comprising the step of maintaining the pressure in said chamber constant independently from the different values of the selectively used probe hoses; said step of maintaining said pressure constant comprising the step of so selecting the diameter of the selectively used probe hoses that said pressure remains constant.

2. In a gas examining apparatus including a gas examining means; a chamber communicating with the gas examining means; a gas pump communicating with the chamber; and probe hoses of given length values and quantity values selectable for attachment to said chamber for introducing into the apparatus gas to be examined; said chamber being arranged upstream of said gas examining means as viewed in the direction of gas flow; the improvement comprising means for maintaining the pressure in said chamber constant independently from said values of the probe hoses utilized; said means for maintaining said pressure constant comprising the selection of the inner diameter of each said probe hose such that the flow rate of gas through each probe hose is the same when operatively attached to said chamber.

3. A gas examining apparatus as defined in claim 2, further comprising a conduit means coupling said chamber to said gas examining means; said conduit means containing a throttle and a shut-off valve immediately adjoining said throttle as viewed in the direction of gas flow in said conduit means; said shut-off valve having a closed position in which it interrupts communication between said chamber and said gas examining means.

4. In a gas examining apparatus including a gas examining means; a chamber communicating with the gas examining means; a gas pump communicating with the chamber; and probe hoses of given length values of quantity values selectable for attachment to said chamber for introducing into the apparatus gas to be examined; said chamber being arranged upstream of said gas examining means as viewed in the direction of gas flow; the improvement comprising means for maintaining the pressure in said chamber constant independently from said values of the probe hoses utilized; and a conduit means coupling said chamber to said gas examining means; said conduit means containing a throttle and a shut-off valve immediately adjoining said throttle as viewed in the direction of gas flow in said conduit means; said shut-off valve having a closed position in which it interrupts communication between said chamber and said gas examining means; said throttle and said shut-off valve constituting a one-piece structural unit.

5. A gas examining apparatus as defined in claim 4, wherein said means for maintaining said pressure constant comprises conduit means coupling said gas pump to said chamber and an adjustable throttle valve in said conduit means for regulating the pressure in said chamber.

6. A gas examining apparatus as defined in claim 4, wherein said means for maintaining said pressure constant comprises an adjustable throttle valve connected between each probe hose and said chamber for regulating the pressure in said chamber.

7. A gas examining apparatus as defined in claim 2 or 4, wherein the volume of said chamber is less than 3 cm$^3$.

8. A gas examining apparatus as defined in claim 2 or 4, further comprising a conduit means coupling said chamber to said gas examining means; and an adjustable throttle arranged in said conduit means.

9. A gas examining apparatus as defined in claim 2 or 4, wherein a plurality of probe hoses of different lengths are permanently connected to said chamber with the intermediary of respective shut-off valves.

10. A gas examining apparatus as defined in claim 2 or 4, wherein said gas examining means comprises a mass spectrometer.

11. A gas examining apparatus as defined in claim 2 or 4, wherein said gas pump is a vacuum pump.

12. A gas examining apparatus as defined in claim 2 or 4, wherein said gas pump is a delivery pump.

* * * * *